US012773578B2

(12) United States Patent
Labarbe et al.

(10) Patent No.: US 12,773,578 B2
(45) Date of Patent: Oct. 27, 2026

(54) COMPUTER IMPLEMENTED METHOD FOR REDUCING THE RISK OF INTERRUPTING AN IRRADIATION TREATMENT SESSION DUE TO A DEVIATION FROM A PLANNED VALUE OF AN OPERATING PARAMETER OF A PARTICLE ACCELERATING SYSTEM

(71) Applicant: ION BEAM APPLICATIONS, Louvain-la-neuve (BE)

(72) Inventors: Rudi Labarbe, Louvain-la-neuve (BE); Lucian Hotoiu, Louvain-la-neuve (BE); Arnaud Pin, Louvain-la-neuve (BE)

(73) Assignee: Ion Beam Applications, Louvain-la-neuve (BE)

( * ) Notice: Subject to any disclaimer, the term of this patent is extended or adjusted under 35 U.S.C. 154(b) by 566 days.

(21) Appl. No.: 18/313,712

(22) Filed: May 8, 2023

(65) Prior Publication Data

US 2023/0364446 A1 Nov. 16, 2023

(30) Foreign Application Priority Data

May 11, 2022 (EP) .................................... 22172682

(51) Int. Cl.
*A61N 5/10* (2006.01)

(52) U.S. Cl.
CPC ........... *A61N 5/1075* (2013.01); *A61N 5/103* (2013.01); *A61N 5/1043* (2013.01); *A61N 5/1067* (2013.01); *A61N 5/1071* (2013.01)

(58) Field of Classification Search
None
See application file for complete search history.

(56) References Cited

U.S. PATENT DOCUMENTS 10,456,598 B2 10/2019 Boisseau et al.
2020/0298020 A1 9/2020 Goebel et al.
(Continued)

FOREIGN PATENT DOCUMENTS

EP 2116277 A1 11/2009
EP 2833970 B1 5/2016
(Continued)

OTHER PUBLICATIONS

Extended European Search Report in counterpart European Patent Application No. 22172682.1, mailed Oct. 24, 2022, 5 pages.

*Primary Examiner* — Eliza W Osenbaugh-Stewart
(74) *Attorney, Agent, or Firm* — Finnegan, Henderson, Farabow, Garrett & Dunner, LLP

(57) ABSTRACT

A computer implemented method for optimizing tolerance values of operating parameters of a particle accelerating system allowing a plurality of beamlets of particles accelerated along an irradiation axis, to deposit doses by pencil beam scanning into a structure of interest of a patient according to a treatment plan. The method calculates the dose (rate) volume histograms for a statistically representative number N of values randomly selected within a defined confidence level in preselected tentative statistical distributions of the operating parameters and compares the obtained calculated dose (rate) volume histogram with an acceptable band of variation of a target dose (rate) volume histogram. Once a tentative statistical distribution yields N calculated dose (rate) volume histograms which all fall within the acceptable band of variation, it is set as the final statistical distribution, and the particle accelerating system can be programmed with the final statistical distribution.

14 Claims, 6 Drawing Sheets

(56) References Cited

U.S. PATENT DOCUMENTS

| | | | | |
|---|---|---|---|---|
| 2020/0353288 | A1 | 11/2020 | Shaw et al. | |
| 2022/0161062 | A1* | 5/2022 | Adamson | G16H 40/63 |
| 2023/0372736 | A1* | 11/2023 | Duan | A61N 5/103 |

FOREIGN PATENT DOCUMENTS

| | | | |
|---|---|---|---|
| EP | 3222322 | A1 | 9/2017 |
| EP | 3375484 | A1 | 9/2018 |
| EP | 3498336 | A1 | 6/2019 |
| EP | 3932481 | A1 | 1/2022 |
| EP | 3932482 | A1 | 1/2022 |
| WO | WO 2011/162021 | A1 | 12/2011 |
| WO | WO 2020/249565 | A1 | 12/2020 |

* cited by examiner

COMPUTER IMPLEMENTED METHOD FOR REDUCING THE RISK OF INTERRUPTING AN IRRADIATION TREATMENT SESSION DUE TO A DEVIATION FROM A PLANNED VALUE OF AN OPERATING PARAMETER OF A PARTICLE ACCELERATING SYSTEM

CROSS REFERENCE TO RELATED APPLICATIONS

This application claims priority of European patent application no. 22172682.1 filed on May 11, 2022, which is incorporated herein by reference in its entirety.

TECHNICAL FIELD

The present disclosure relates to the general field of treatment of tumoral cells by irradiation with accelerated particles, such as protons. In particular, the present disclosure provides a method for setting the operating parameters of a given particle accelerating system ensuring that the given particle accelerating system can deliver within a predefined confidence level beamlets of accelerated particles fulfilling the requirements of a treatment plan (TP) comprised within an acceptable band of variation (BV). This method is advantageous in that it reduces to within the predefined confidence level the risk of having to suddenly interrupt a patient irradiation session because the given particle accelerating system failed to deliver one or more beamlets satisfying the TP within the acceptable band of variation.

BACKGROUND

Radiation therapy with particles or waves, such as protons beams, electron beams, heavy ions beams, x-rays, y-rays, and the like, has become an essential tool for treating patients with tumors.

Pencil beam scanning (PBS) is a technique consisting of steering beamlets of charged particles towards a target comprising tumoral cells defining a structure of interest. PBS reduces unnecessary radiation exposure to surrounding non-cancerous cells by shaping the area being treated to mirror the tumor geometry of the structure of interest. Pencil beam scanning can treat a tumor with a single beam composed of various beamlets or with multiple beams of different orientations each composed of various beamlets, sometimes called intensity modulated proton therapy (IMPT). Beside the geometry of the target, PBS allows local tuning of the parameters of the beamlets depending on the position within the target. The parameters can include a position and a monitor (provided as a monitor unit) of each beamlet as well as the scanning sequence of the beamlets, with starting time and end time of each beamlet.

Since both tumoral cells and healthy cells are damaged by such radiations, a major challenge in cancer treatment is to define a treatment plan (TP) ensuring that the tumoral cells are effectively destroyed or killed, while sparing as much as possible the healthy cells, in particular those adjacent to the tumoral cells. A first step of a treatment plan is the capture of images of the tumoral region by CT-scan. Based on these images, an oncologist identifies the right targets and determines the locations and doses to be deposited to kill the tumoral cells. Such plan must satisfy multiple, often competing, parameters, and is therefore quite complex. For this reason, treatment planning is generally carried out with a computer.

The treatment plan (TP) generally comprises a definition of an array of n beamlets (bi), including values of planned parameters comprising,

- a planned position of each beamlet (Xpi), defining the positions of spots aimed at by each beamlet which depends inter alia on the positions, sizes, and geometries of the tumoral cells within the structure of interest,
- a planned monitor unit (MUpi) of each beamlet, which relates to the number of particles going through the nozzle of the particle accelerating system and which must reach a given spot in the structure of interest.
- a planned beamlet scanning sequence over the planned positions (Xpi); this is useful, since a beamlet deposits a dose into the corresponding spot, but can also deposit lower doses into neighbouring spots, which cannot be neglected when accounting the overall doses deposited in each spot; this is particularly true for flash treatment described more in detail infra.

The treatment plan must ensure that, at the end of the treatment, a total target dose greater than or equal to a minimum target dose has been delivered to the tumoral cells forming the target effective for destroying/killing the tumoral cells. This can be defined by a target dose volume histogram (=tDVH), for the structure of interest. An example of tDVH is represented with a solid line in FIG. 1(*a*), showing a graph plotting the volume (%) of the structure of interest which must receive at least a target dose as defined by the abscissa of the curve of FIG. 1(*a*). The oncologist also defines an acceptable band of variation (BV) within which a dose volume histogram (DVH) can deviate from the targets tDVH and represented in FIG. 1(*a*) with dashed lines.

Historically, treatment plans by radiation therapy included the delivery of radiation doses to the treated cells at a conventional dose deposition rate (CDR) lower than 1 Gy/s. With rare exceptions, current radiation therapy facilities deliver dose-rates around 0.1 Gy/s and most clinical protocols involve daily delivery of several target fraction doses of 2 to 15 Gy cumulated to reach the total target dose which often exceeds the tolerance limit of normal tissues located in the radiation field, thus damaging them together with the tumoral cells. Recently, it has been observed that a same dose had different effects on healthy cells but not on tumoral cells when deposited at conventional dose deposition rates (CDR) or at ultra-high dose deposition rate (HDR); HDR can be one or more orders of magnitude larger than conventional dose deposition rates (CDR) usually applied. Deposition of a charge at ultra-high dose deposition rates (HDR) is also referred to as FLASH-radiotherapy (=FLASH-RT). It has been demonstrated experimentally on animals and on various organs, that ultra-high rate dose deposition at HDR can significantly spare healthy tissues in comparison with conventional deposition of a same dose at CDR and, at the same time, tumoral cells respond same or even better to HDR deposition than to CDR deposition. For example, FLASH-RT reportedly elicits in mice a dramatic decrease of the incidence of lung fibrosis, of memory loss subsequent to brain irradiation, and of necrosis of the small intestine whilst keeping the anti-tumor efficiency unchanged. Such specific normal tissue sparing has been confirmed in large animals and a patient with cutaneous lymphoma has already been treated with FLASH-RT.

The dose rate distribution in tissue can be defined by a target dose rate volume histogram (=tDRVH), for the structure of interest. An example of tDRVH is represented with a solid line in FIG. 1 (*b*), showing a graph plotting the volume (%) of the structure of interest which must receive a target dose rate or higher for the tDRVH as defined by the abscissa of the curves of FIG. 1(*b*). The oncologist also defines an acceptable band of variation (BV) within which a dose rate volume histogram (DRVH) can deviate from the target tDRVH and represented in FIG. 1(*b*) with dashed lines.

The dose volume histogram (DVH) and dose rate volume histogram (DRVH) are cumulative histograms. There are other ways, however, of representing the distribution of doses or dose rates. For example, FIG. 1(*c*) shows a differential dose rate histogram (DDRH) indicating the number of voxels in a structure of interest which receive a dose at the corresponding dose rate indicated in the abscissa. The acceptable band of variation (BV) is represented with dashed lines, and the long-dashed line is actual values of differential dose rate histogram (=aDDRH) measured during a treatment session. Other representations are possible. All types of representations of the desired doses and dose rates distributions in a structure of interest a treatment plan must achieve are herein collectively referred to as "dose distribution histograms (DDH)" and "dose rate distribution histograms (DRDH)." The expression "dose (rate) distribution histogram (D(R)DH)" is also used herein for sake of conciseness to include both DDH and DRDH.

Fulfilling the planned beamlet scanning sequence may require defining a planned starting time and a planned end time for each beamlet. This is particularly useful for FLASH-RT.

A treatment plan system (TPS) defines beamlets parameters including positions of beamlets (Xj), monitoring units (MUj) and spots sequence to achieve a treatment plan (TP). A translation system (=TS) determines the operating parameters of a given particle accelerating system required for implementing the beamlets parameters, taking into account limits of the particle accelerating system. This is described, e.g., in US20200298020, EP3932482, and EP3932481. The operating parameters are determined to ensure that the beamlets delivered by the given particle accelerating system will deposit doses into the structure of interest according to the target dose (rate) distribution histogram (D(R)DH) within the acceptable bands of variation (BV). The conversion of the TP into machine operating parameters ensures that a treatment session can be completed within the treatment plan, and not interrupted because at some point, the random variability of some operating parameters leads the beamlets actually delivered by the particle accelerating system to yield a D(R)DH which falls outside of the acceptable band of variation (BV).

The nominal value of the operating parameters defined in the plan may not be precisely met by a given particle accelerating system. The operating parameters values at which the particle accelerating system will actually be operating follow instead specific statistical distributions (Tj) as illustrated in FIG. 2, characterized by an average value (μj) (which is the nominal value defined by the treatment plan) and a variance ($\sigma j^2$) representing the random variability of the treatment machine. This means that, even if the TS correctly converts the treatment plan (TP) into operating parameters to ensure that the given particle accelerating system delivers beamlets characterized by the average values (μj), the actual values of the operating parameters on a specific treatment session will be spread around the average value (RD over the statistical distribution curve (Tj) (shown in FIG. 2). It is therefore clear that during a treatment session, the operating parameters will deviate from the average values (μi) following the distributions thereof. In some cases, values of the actual operating parameters of the beamlets may yield dose (rate) distribution histogram (D(R)DH) extending beyond (outside) the corresponding acceptable bands of variation (BV), and the treatment session must be interrupted despite a correct TP conversion by the TS. If a treatment session does not proceed as planned, it can be dangerous for the patient.

Some particle accelerating systems are equipped with a monitoring device measuring the actual operating parameters of the beamlets as they are being delivered through a nozzle. EP2116277, EP3375484, U.S. Ser. No. 10/456,598, EP3222322, WO2020249565, and EP2833970 describe examples of devices for in situ monitoring and verification of a selection of operating parameters of the beamlets delivered by a particle accelerating system. In case the operating parameters of one or more beamlets monitored differ from the planned values (which is likely to happen), there is a risk that the corresponding dose (rate) distribution histogram (D(R)DH) extend beyond the acceptable band of variation (BV). Should this be the case, the treatment session must be stopped. This is very uncomfortable for the patient who may have to come back later to complete the treatment session, depending on the usually tight schedule of the particle accelerating system. It is therefore useful to take the distributions of the operating parameters into consideration to ensure that a treatment session can be completed within a predefined confidence level (CLj) with all beamlets yielding the dose (rate) distribution histogram (D(R)DH) in accordance with the treatment plan.

Furthermore, an actual value of an operating parameter differing from the corresponding planned value does not necessarily mean that the corresponding dose (rate) distribution histogram (D(R)DH) extends beyond the acceptable band of variation. With the calculating power of processors available to date, it is not thinkable of calculating for each measurement of the actual values of the operating parameters the corresponding calculated dose (rate) distribution histogram (D(R)DH) to decide whether or not to interrupt the treatment session because one actual value differs from the planned values of the operating parameters.

EP3498336 describes a system and method for treating a dummy (mannequin) and evaluating a dose volume histogram (DVH) by dosimetry before applying the treatment to a patient. This technique clearly reduces the risk of having to interrupt a treatment session, but it also requires blocking a particle accelerating system for the time required to make the tests, during which it cannot be used for treating a patient. Furthermore, a dosimetric tolerance can translate into different machine tolerance levels for spots at different locations or with different monitoring units (Mus) (e.g., spot on the edge of the structure of interest may have a higher constraint on position accuracy than spots at the center of the structure). It is also not obvious how to translate a dose rate tolerance into a tolerance for each spot in the spot map. In some places it is more useful to check that the irradiation is in FLASH-RT mode than in other places. The tolerances on the dose rate may also be different between positions in the tissue. For example, FLASH-RT could be required at the edges of the structure of interest, where tumoral cells are flanked by healthy cells which must be spared.

To date, most methods for ensuring that the operating parameters will yield the desired dose (rate) distribution histogram (D(R)DH) is a posteriori, i.e., by measuring the treatment properties of the beamlets delivered by the particle accelerating system or, at best, based on dosimetric tests on a dummy (mannequin) performed before treating the patient. There remains a need in the art for a method for determining by calculation, i.e., without having to use precious accelerator time and energy, a set of operating parameters of the particle accelerating system to be used, yielding within a predefined confidence level the desired dose (rate) distribution histogram (D(R)DH) within the acceptable band of variation (BV).

SUMMARY

The present disclosure provides a method implemented by a computer for optimizing tolerance values of operating parameters of a particle accelerating system allowing a beam formed by a plurality of beamlets of particles accelerated along an irradiation axis (Z), to deposit doses by pencil beam scanning (=PBS) into a structure of interest of a patient according to a treatment plan (=TP), the computer implemented method comprising, (a) providing an input comprising
  - the treatment plan (=TP) including a definition of an array of beamlets (bi), characterized by planned parameters, including,
    - a planned position (Xpi) of each beamlet (bi) on a plane (X, Y) normal to the irradiation axis (Z),
    - a planned monitor unit (MUpi) of each beamlet,
    - a planned beamlet scanning sequence over the planned positions (Xpi),
  - a planned starting time (t0*pi*) and end time (t1*pi*) at which each beamlet is to be delivered,
  - a definition of the structure of interest, defining one or more tissues being traversed by a number of the beamlets (bi),
  - values of one or more target dose (rate) distribution histograms (=tD(R)DH) including a dose distribution histogram (=tDDH) and/or a target dose rate distribution histogram (=tDRDH), for the structure of interest obtained with a treatment with the planned parameters, wherein the dose distribution histogram (DDH) may be a dose distribution volume histogram (DDVH), and the dose rate distribution histogram (DRDH) may be a dose rate distribution volume histogram (DRDVH) or a differential dose rate histogram (DDRH), and
  - acceptable bands of variation (BV) in which the one or more tD(R)DH are allowed to vary, (b) providing a tentative statistical distribution (Tj) of operating parameters of the particle accelerating system centered on corresponding average values (μj) representative of the performance of the particle accelerating system and defining a confidence level (CLj) of the tentative statistical distribution (Tj), wherein the operating parameters comprise,
  - a monitor unit (MUD of each beamlet,
  - a position of each beamlet (Xj), and
  - a starting time (t0*j*) and a end time (t1*j*) of delivery of each beamlet, (c) randomly selecting from the corresponding tentative statistical distributions (Tj) within the predefined confidence levels (CLj) a value (MUij) of the monitor unit, a value (Xij) of the position of the beamlet, and a value (t0*ij*, t1*ij*) of each of the starting time (t0*ij*) and end time (t1*ij*), (d) calculating one or more calculated dose (rate) distribution histograms (=cD(R)DHj−Run x) with the values randomly selected, (e) repeating the last two steps (c), (d) a statistically representative number of times (N) to yield calculated distributions (CDj) characterizing the one or more calculated cD(R)DHj−Run x for all the values randomly selected of the operating parameters, and (f) comparing the calculated distributions (CDj) of the one or more calculated dose (rate) distribution histogram (cD(R)DHj) with the corresponding acceptable bands of variation (BV) and determining whether the calculated distributions (CDj) of the one or more cD(R)DHj are comprised in the corresponding acceptable bands of variation within the pre-defined confidence level (CLj).

In accordance with some embodiments, a final statistical distribution (Tf) can be set with a final confidence level (CLf) to the corresponding operating parameters by a human operator or by a processor as follows, If the calculated distributions (CDj) of the one or more cD(R)DHj are all comprised within the corresponding acceptable bands of variation (BV) with the pre-defined confidence level (CLj), for the given treatment plan (TP), setting the tentative statistical distribution (Tj) as the final statistical distribution (i.e., Tf=Tj) and the confidence level (CLj) as the corresponding final confidence level (CLf=CLj) to define the corresponding operating parameters;

If any one of the one or more calculated dose (rate) distribution histogram (cD(R)DHj) calculated with one set of randomly selected values within the corresponding confidence levels (CLj) of the statistical distribution (Tj) of the operating parameters extends beyond the corresponding acceptable bands of variation (BV), repeating steps (b) to (f),
  - with new tentative statistical distributions (T(j+k)) of the operating parameters and/or
  - selecting new, less ambitious confidence levels (CL(j+k)), until the calculated distributions (CD(j+k)) of the one or more cD(R)DH(j+k) are all comprised within the corresponding acceptable bands of variation (BV), and setting the tentative statistical distribution (T(j+k)) as the final statistical distribution (i.e., Tf=T(j+k)) and setting the corresponding confidence level (CL(j+k) as the final confidence level (CLf=CL(j+k)) to define the corresponding operating parameters.

In accordance with some embodiments, the new tentative statistical distributions (T(j+k)) can have lower standard deviations (σj) than the corresponding tentative statistical distributions (Tj) defined above. The tentative statistical distributions (Tj) of each of the operating parameters may be gaussian distributions, and the value of the confidence level (CLj) can be comprised between 68% and 99.7%, or between 95.5 and 99% of the tentative statistical distribution wherein a confidence level (CLj) of 68% corresponds to μj±σj, a confidence level (CLj) of 95% corresponds to μj±2σj, and a confidence level of 99.7% of the tentative statistical distribution, corresponds to μj±3σj, wherein μj is an average value and σj is the standard deviation of the corresponding tentative statistical distributions, the average values (μj) and standard deviations (σj) of each operational parameter being the same or different for each beamlet (bi).

In accordance with some embodiments, the particle accelerating system can be equipped with a cyclic checker (provided as a cyclic check module) configured to measure at different intervals or continuously actual values of the operating parameters including the monitor unit (MUai), the position (Xai), and of the starting time and end time (t0*ai*, t1*ai*) of the beamlets emitted by the particle accelerating system.

In accordance with some embodiments, the particle accelerating system can also be equipped with a processor configured to compare the actual values of the operating parameters with the corresponding confidence level (CLj), and to stop a treatment session in case one actual value of an operating parameter falls outside of the corresponding confidence level (CLj).

In accordance with some embodiments, the planned parameters also comprise a planned beamlet size (dj) and a planned beam current (Ij), whose respective values (dij, Iij) used for calculating the one or more calculated dose (rate) distribution histograms (=cD(R)DH) are randomly selected within a corresponding tentative statistical distribution (Tj) of the beamlet size (dj) and of the planned beam current (Ij).

In accordance with some embodiments, the calculated distributions (CDj) of the one or more cD(R)DH are defined by a corresponding area comprised in an envelope defined between, on the one hand, a minimum calculated dose (rate) distribution histogram (=cD(R)DHj0) and, on the other hand, a maximum calculated dose (rate) distribution histogram (=cD(R)DHj1). The cD(R)DHj0 is defined by the lowest values of cD(R)DHj calculated with the predefined confidence level (CLj) from the N randomly selected values of the monitor unit (Muij), position (Xij) of the beamlets, and starting time and end time (t0*ij*, t1*ij*) and the cD(R)DHj1 is defined by the highest values of cD(R)DHj calculated with the predefined confidence level (CLj) from the N randomly selected values of the monitor unit (Muij), position (X0*i*) of the beamlets, and starting time and end time (t0*ij*, t1*ij*).

In accordance with some embodiments, the treatment plan includes depositing doses into at least a portion of the structure of interest at ultra-high deposition rates (UHDR) defined as a deposition rate greater than or equal to 1 Gy/s.

The present disclosure also provides an error predictor (provided as an error predicting module) configured to implement the above method, comprising,

- a memory comprising a plurality of tentative statistical distributions (Tj) for each operating parameter centered on a plurality of corresponding average values (Rj),
- a user interface configured to,
  - enter the treatment plan (TP) including one or more target dose (rate) distribution histograms (=tD(R)DH) including the target dose distribution histogram (=tDDH) and/or the target dose rate distribution histogram (=tDRDH), as well as the corresponding acceptable bands of variation (BV),
  - select from the memory or enter a planned starting time (t0*pi*) and end time (t1*pi*) at which each beamlet is to be delivered,
  - select from the memory or enter for each beamlet, a first tentative statistical distribution (Tj) for each operating parameter, including the monitor unit (MUj), the position (Xj) of the beamlet, and starting time and end time (t0*i*, t1*i*), and
  - enter a confidence level (CLj) on the operational parameters,
- a processor configured to,
  - (i) randomly select a value of the monitor unit (MUij), a value of the position (Xij) of the beamlet, values of the starting time and end time (t0*ij*, t1*ij*) comprised within the predefined confidence levels (CLj) of the corresponding tentative statistical distributions (Tj),
  - (ii) calculate one or more of a calculated dose distribution histogram (=cDDHj) and a calculated dose rate distribution histogram (=cDRDHj) with the values randomly selected, and
  - (iii) repeat steps (i) and (ii) a statistically representative number of times to yield the calculated distributions (CDj) of the calculated cDDHj and cDRDHj for each beamlet.

In accordance with some embodiments, the processor can be further configured, in case any one of the one or more of the calculated distributions (CDj) of cDDHj and cDRDHj are not comprised within the corresponding acceptable bands of variation with the pre-defined confidence level (CLj), to repeat steps (i) to (iii) with new tentative statistical distributions (T(j+k)) of the operating parameters, until the calculated distributions (CDj+k) of the one or more of cDDHj+k and cDRDHj+k are both comprised within the corresponding acceptable bands of variation with the predefined confidence level (CLj).

BRIEF DESCRIPTION OF THE FIGURES

For a fuller understanding of the nature of the present disclosure, reference is made to the following detailed description taken in conjunction with the accompanying drawings in which.

DETAILED DESCRIPTION

The present disclosure provides a computer implemented method and an error predicting module which considerably reduce the risk of carrying out a treatment session which does not respect a corresponding treatment plan, for reasons of equipment.

The present disclosure also provides a computer implemented method for optimizing tolerance values of operating parameters of a particle accelerating system allowing a beam formed by a plurality of beamlets of accelerated particles to deposit doses by pencil beam scanning (=PBS) into a structure of interest of a patient according to a treatment plan (=TP). The method allows determining the confidence level (CLj) for a given particle accelerating system to deliver beamlets which will fulfil the TP as a function of a set of operating parameters. If the confidence level obtained is too low, an alternative set of operating parameters needs be evaluated. These and other advantages of the present disclosure are presented below.

Method for Optimizing Tolerance Values of Operating Parameters

Figure 6:
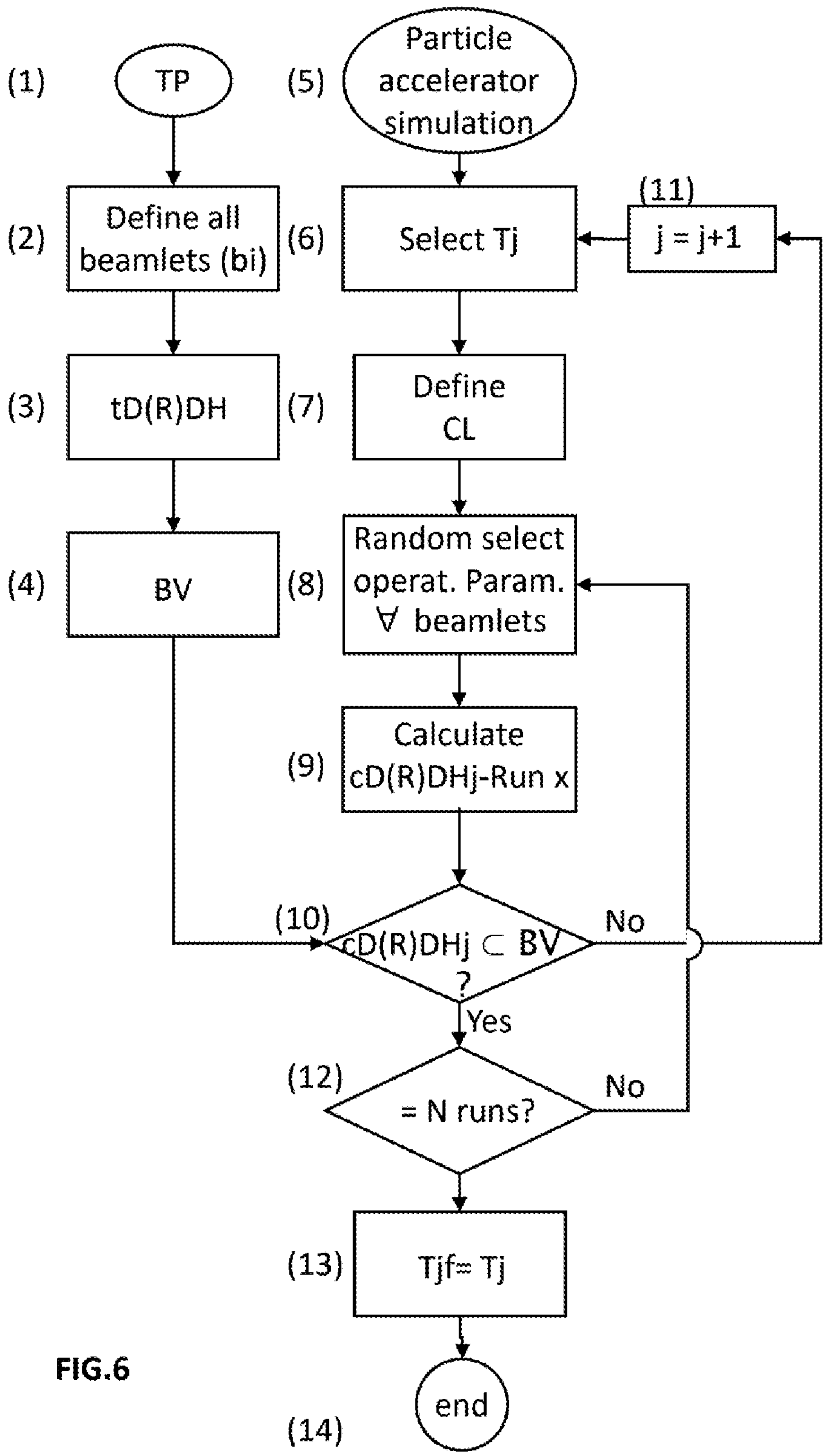
FIG. 6 shows a flowchart with various steps of a method of the present disclosure.

The present disclosure provides a method implemented by a computer for optimizing tolerance values of operating parameters of a particle accelerating system allowing a beam formed by a plurality of beamlets of particles accelerated along an irradiation axis (Z), to deposit doses by pencil beam scanning (=PBS) to a patient according to a treatment plan (=TP). The particles may be protons, but they can be electrons, heavy ions beams, but also waves formed by accelerated particles interacting with a converting material, such as x-rays (or y-rays). As illustrated in FIG. 6, the computer implemented method receives the input of a number of values of planned parameters. These can be provided by a treatment plan (TP) including the following planned parameters,

- a planned position (Xpi) of each beamlet (bi) on a plane (X, Y) normal to the irradiation axis (Z),
- a planned monitor unit (MUpi) of each beamlet,
- a planned beamlet scanning sequence over the planned positions (Xpi), The method also receives a planned starting time (t0*pi*) and end time (t1*pi*) at which each beamlet is to be delivered. This is particularly useful in case of FLASH-RT. The starting and end times may or may not be part of the TP.

A structure of interest is defined, characterizing one or more tissues, of the patient, being traversed by or interacting with the beamlets (bi). The structure of interest comprises the target comprising the tumoral cells to be killed, but also healthy tissues traversed or somehow touched by one or more beamlets. These include, for example, the tissues located upstream from the target along the irradiation axis (Z), i.e., between the nozzle of the particle accelerating system and the target, or also the tissues adjacent to and surrounding the target.

Figure 1A:
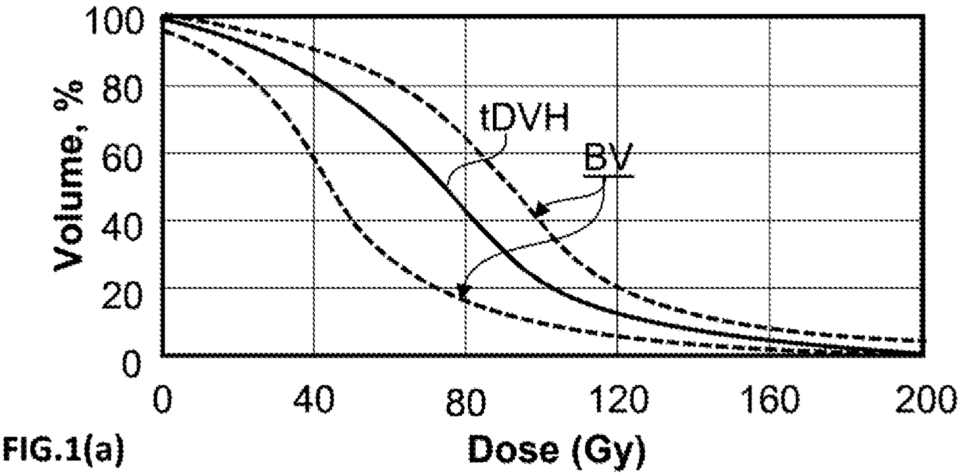
FIGS. 1(*a*) to 1(*c*) show examples of tDVH, tDRVH, and tDDRH curves with their corresponding acceptable bands of variation (BV).
Figure 1B:
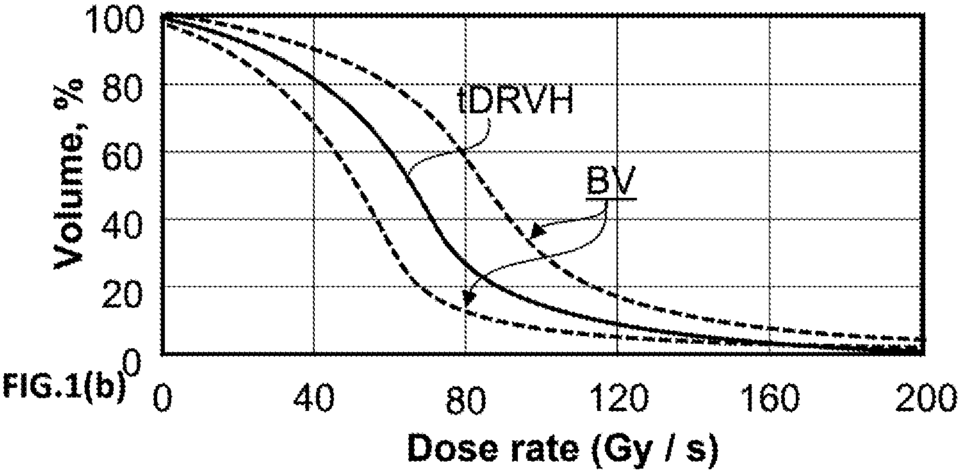
Figure 1C:
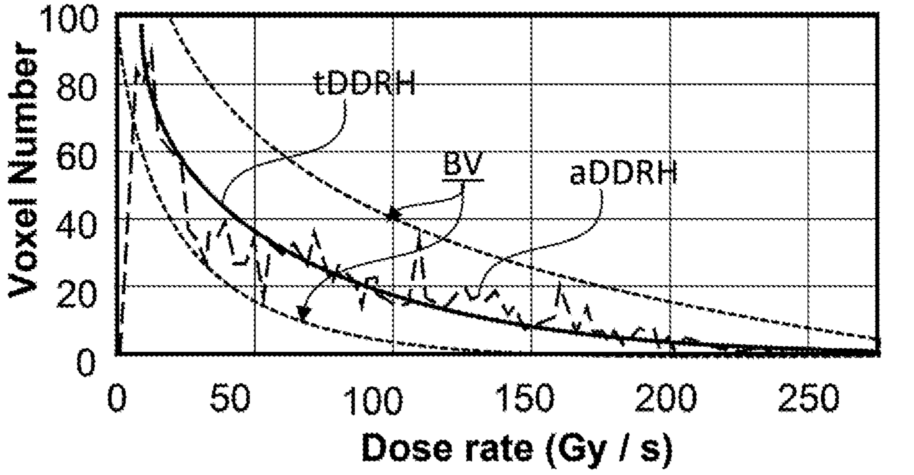
Figures 4A, 4B, 4C:
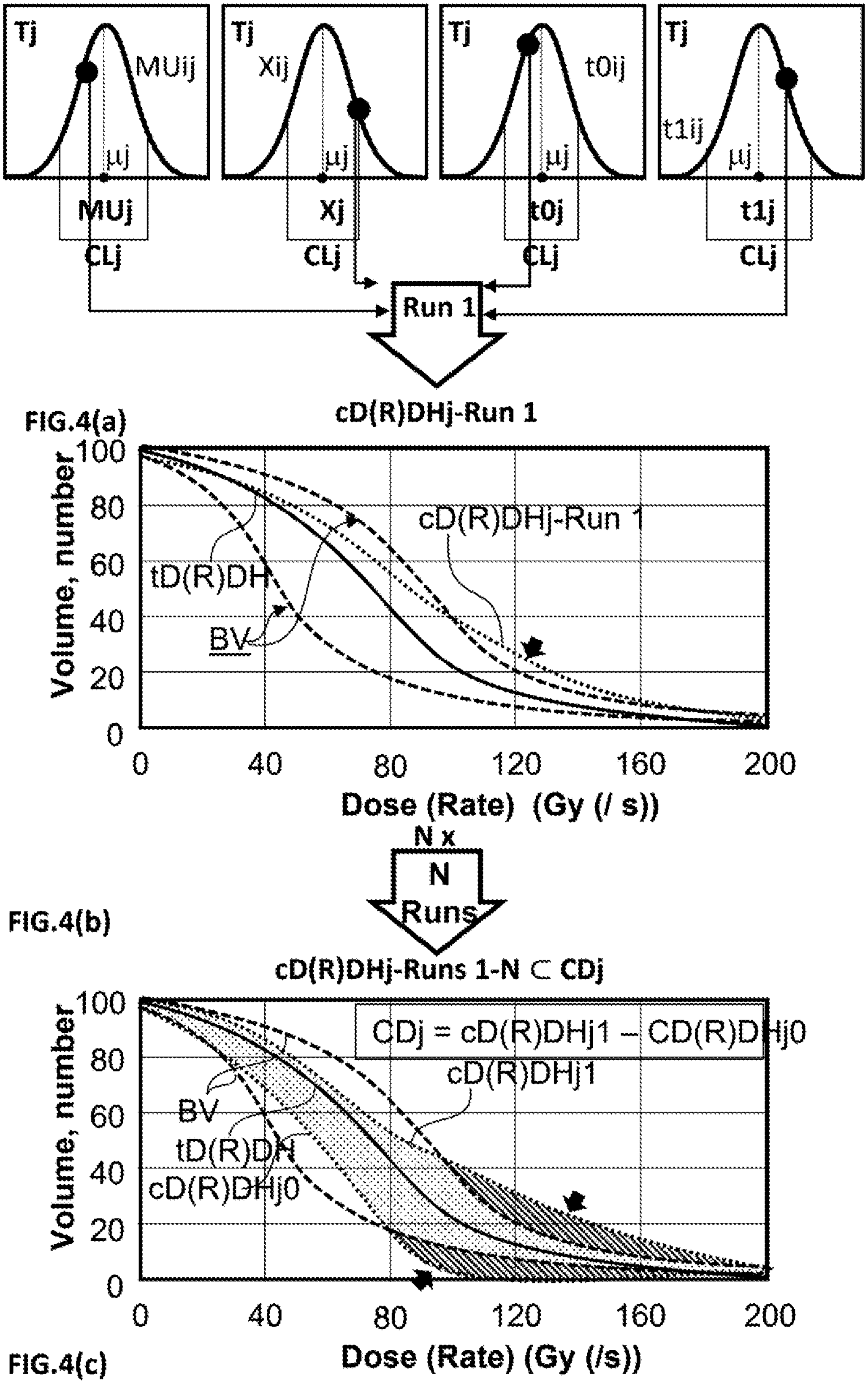
FIGS. 4(*a*) to 4(*c*) show various steps of one embodiment of the present disclosure, with a negative result.

An objective of the treatment is to yield at the end of a session, given values of a target dose (rate) distribution histogram (tD(R)DH) for the structure of interest, within an acceptable band of variation (BV) in which a target dose (rate) volume histogram tD(R)VH is allowed to vary. As shown in FIGS. 1(*a*) to 1(*c*), tD(R)DH can include for example a target dose volume histogram (=tDVH) (show in FIG. 1(*a*)), a target dose rate volume histogram (=tDRVH) (shown in FIG. 1(*b*)), or a target differential dose rate histogram (tDDRH) (shown in FIG. 1(*c*)). Note that other histogram representations are possible and included in the term tD(R)DH, to display the information on the dose and dose rate distributions. FIGS. 1(*a*) to 1(*c*) show examples of tDVH, tDRVH, and tDDRH represented by the solid lines, as well as of the corresponding acceptable bands of variation (BV) represented by the area comprised between the dashed lines. Similar acceptable bands of variation can be defined for any type of alternative dose (rate) distribution histograms (D(R)DH) representations. If the beamlets delivered by the particle accelerating system achieve a dose distribution histogram (DDH) and a dose rate distribution histogram (DDRH) comprised within the acceptable band of variation as shown in FIG. 1(*c*), the session is successful. In case the DDH or DRDH falls outside of the acceptable band of variation (BV), the treatment session must be interrupted, to the great discomfort of the patient who must wait for a free slot in the particle accelerator system's schedule to resume the treatment session. The present disclosure allows anticipating within a given confidence level the occurrence of such an event, as shown in FIGS. 4(*b*) and 4(*c*) and modifying the tentative statistical distribution of operating parameters of the particle accelerating system to reduce the probability of having to interrupt a session.

FIG. 1(*c*) includes the actual values of the differential dose rate distribution histogram (aDDRH) obtained upon measuring the beamlets parameters during a treatment session (shown as long-dashed line). It can be seen that the curve aDDRH in FIG. 1(*c*) is fully enclosed within the acceptable band of variation (BV). The treatment session was therefore successful. Had the curve aDDRH extended beyond the acceptable band of variation (BV), however, the treatment session would have had to be interrupted. In order to decrease the risk of having to interrupt a treatment session because of the actual dose (rate) distribution histograms (D(R)DH) falling outside of the acceptable band of variation, the present disclosure implements the following actions with a computer.

Figure 3A:
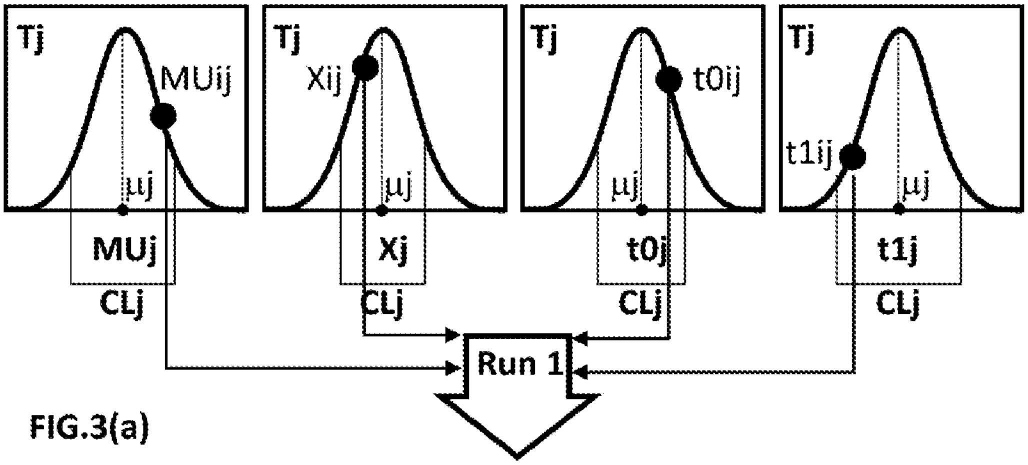
FIGS. 3(*a*) to 3(*c*) show various steps of one embodiment of the present disclosure, with a positive result.
Figure 3B:
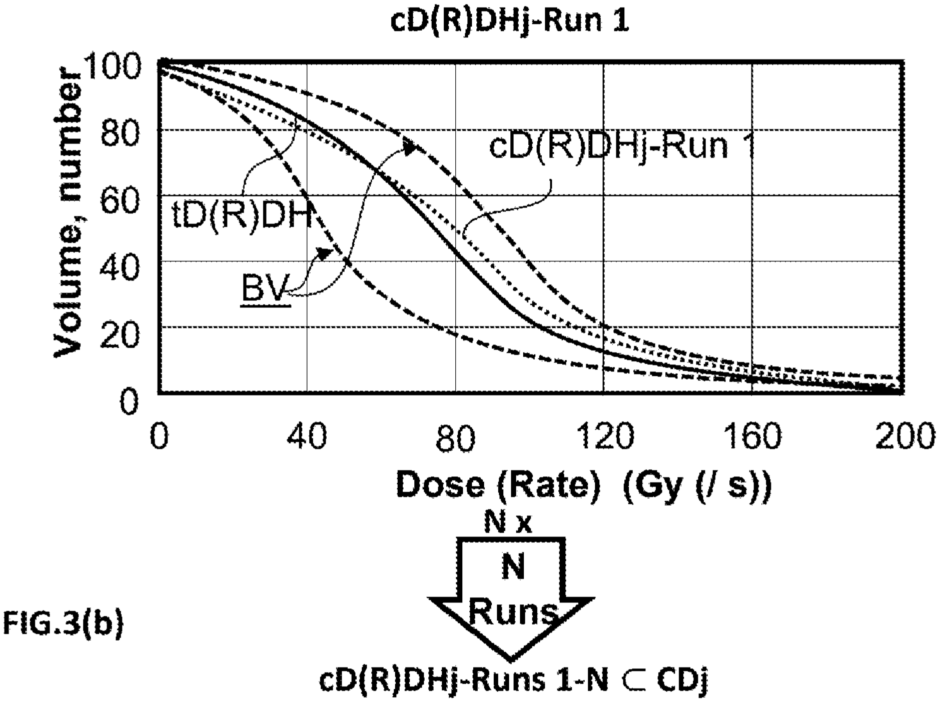
Figure 3C:
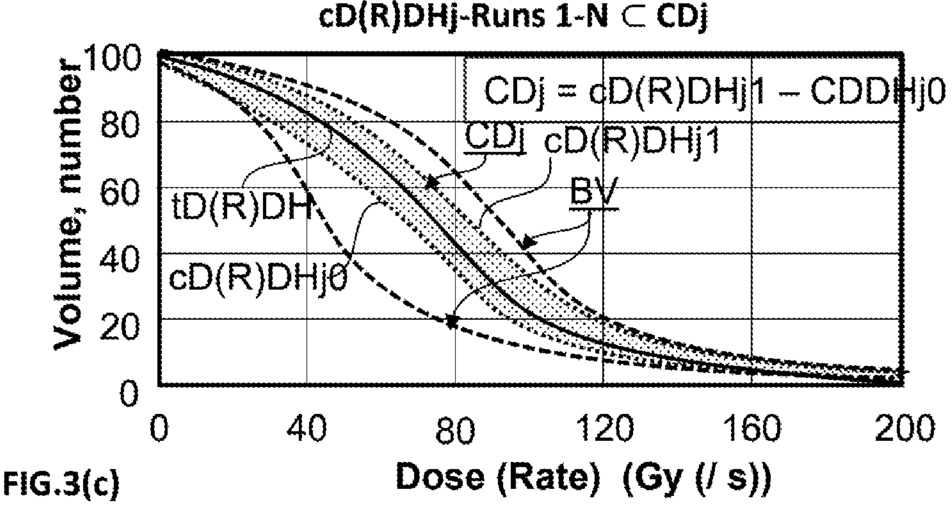

First, as shown in FIGS. 3(*a*) and 4(*a*), a tentative statistical distribution (Tj) is selected of operating parameters (MUj, Xj, t0*j*, t1*j*) of the particle accelerating system centered on corresponding average values (μj) representative of the performance of the particle accelerating system. A confidence level (CLj) of the tentative statistical distribution (Tj) of each of the operating parameters is defined. The operating parameters include:

- monitor unit (MUj) of each beamlet,
- position of each beamlet (Xj), and
- starting time (t0*j*) and end time (t1*j*) of delivery of each beamlet.

The selection of tentative statistical distributions (Tj) is based on the performance of the particle accelerating system and is expected to generate a beam delivering the beamlets scanning sequence and generating calculated dose volume histograms (=cDVHj) and calculated dose rate volume histograms (=cDRVHj) in the structure of interest that are comprised within the acceptable band of variation (BV). For example, a treatment plan system (TPS) can determine average values (μj) achievable by the particle accelerating system which would yield the desired cDVH and cDRVH. The actual operating parameters of the treatment machine on a specific day, however, are not restricted to the corresponding average values (μj) but are distributed generally over a Gaussian curve, varying from day to day or during the course of a day (shown in FIG. 2). The resulting calculated dose (rate) distribution histograms (cD(R)DH) will therefore vary depending on the actual values of the operating parameters at the specific time of the treatment and must therefore be calculated taking account of the distribution. It would not be practical to consider all the possible values of each operating parameter defined by the corresponding distribution curves. A confidence level (CLj) can be defined, restricting the distribution to boundaries which are considered as acceptable. For example, the confidence level can be defined with respect to the standard deviation (σj), such as for example, μj±nσj, with n=1 to 3 (shown in FIG. 2).

A value (MUij) of the monitor unit, a value (Xij) of the position of the beamlet, and values (t0*ij*, t1*ij*) of starting time (t0*ij*) and end time (t1*ij*) are randomly selected from the corresponding tentative statistical distributions (Tj) within the corresponding confidence levels (CLj) as shown with the black circles in the Gaussian distribution curves (Tj) of FIGS. 3(*a*) and 4(*a*). The values are selected within the confidence level (CLj) previously defined.

Figures 5A, 5B, 5C, 5D:
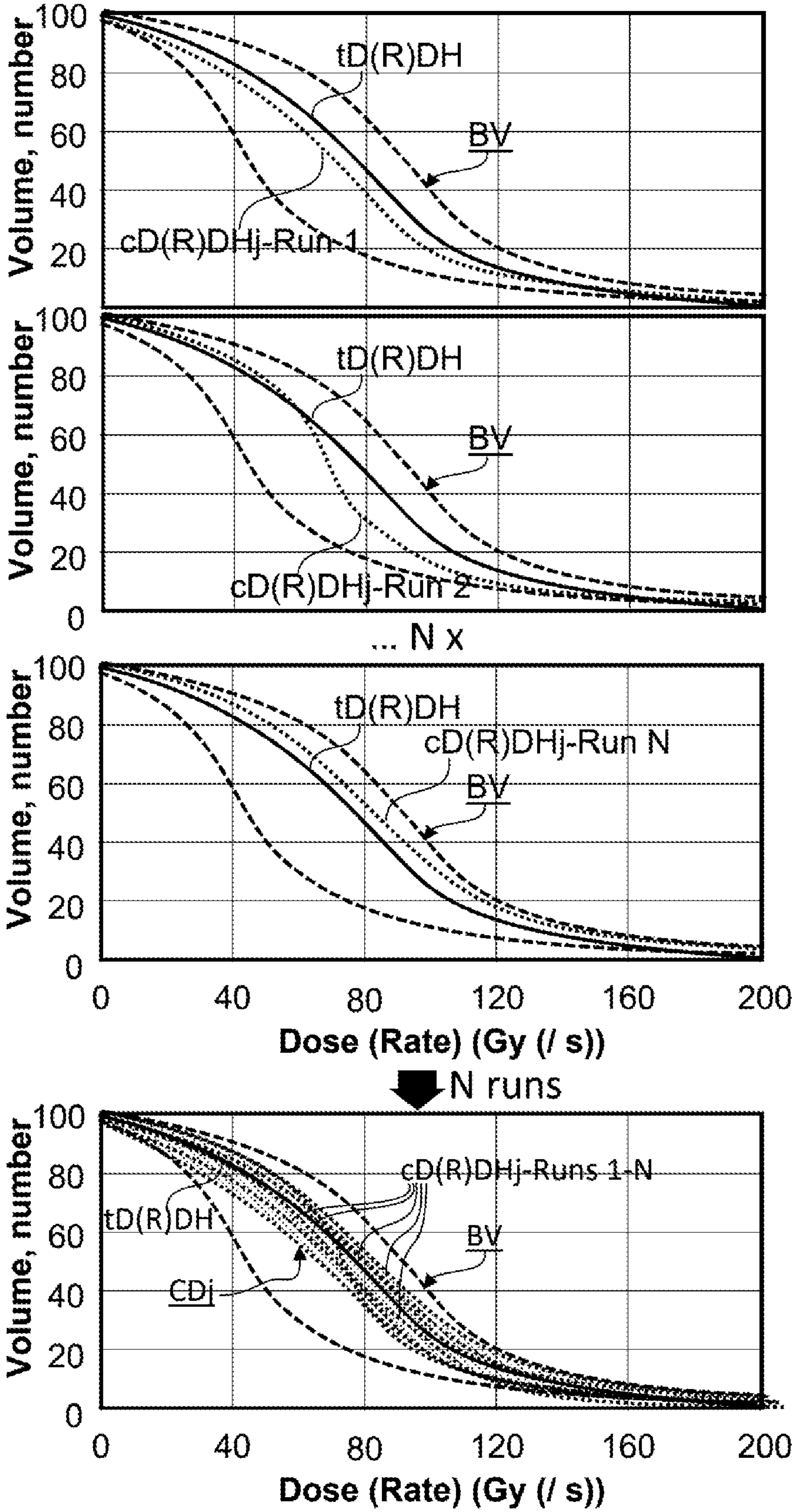
FIGS. 5(*a*) to 5(*d*) show N runs of calculations yielding calculated distributions (CDj) of the calculated cD(R)DHj shown in FIGS. 3(*b*) and 3(*c*).

As shown in FIG. 5(*a*), in a first Run (=Run 1), the calculated dose (rate) distribution histogram (=cD(R)DHj) is calculated with the values randomly selected. If the calculated cD(R)DHj is enclosed within the corresponding acceptable band of variation, new values of the operating parameters are randomly selected from the tentative statistical distributions (Tj) and the corresponding cD(R)DHj is calculated in a second Run (=Run 2) as illustrated in FIG. 5(*b*). These operations are repeated a statistical number of times (N) as illustrated in FIG. 5(*c*), "Run N", as long as the calculated cD(R)DH−Run x are enclosed within the acceptable band of variation (BV). After N runs, the N curves "cD(R)DHj−Run x" with x=1 to N define in combination a calculated distribution (CDj), represented in FIGS. 3(*b*), 3(*c*), 4(*b*), 4(*c*), and 5(*d*) by the shaded areas bounded by the dotted lines of cD(R)DHj0 and cD(R)DHj1.

If, on the other hand, any one of the cD(R)DHj–Run x calculated extends beyond the acceptable band of variation (BV), it could be concluded that there would be a risk higher than the predefined confidence level (CLj) of having to interrupt a treatment run with the operating parameters of the particle accelerating system according to the tentative statistical distributions (Tj). A new tentative statistical distribution (T(j+1)) of the operating parameters is then selected, and the cD(R)DH(j+1) is calculated in a new series of N Runs with randomly selected values of the new tentative statistical distributions (T(j+1)) at each successive Run. This operation is repeated with new tentative statistical distributions (T(j+k)) until the corresponding calculated distributions (CD(j+k)) are entirely comprised within the acceptable band of variation (BV).

Besides the planned position (Xpi), the planned monitor unit (MUpi), the planned beamlet scanning sequence over the planned positions (Xpi), and the planned starting time (t0*pi*) and end time (t1*pi*), the planned parameters can also comprise a planned beamlet size (dj) and a beam current (Ij), whose values (dij, Iij)) used for calculating the calculated dose (rate) distribution histogram (=cD(R)DHj) are randomly selected within a corresponding tentative statistical distribution (Tj) of the beamlet size (dj) and beam current (Ij).

The calculated distributions (CDj) of the cD(R)DHj can be defined by a corresponding area comprised between,

- a minimum calculated dose (rate) distribution histogram (=cD(R)DHj0) and,
- a maximum calculated dose (rate) distribution histogram (=cD(R)DHj1), wherein

- cD(R)DHj0 is defined by the lowest values of cD(R)DHj calculated with the predefined confidence level (CLj) from the N randomly selected values of the monitor unit (Muij), position (Xij) of the beamlets, and starting time and end time (t0*ij*, t1*ij*) and wherein
- cD(R)DHj1 is defined by the highest values of cD(R)DHj calculated with the predefined confidence level (CLj) from the N randomly selected values of the monitor unit (Muij), position (X0*i*) of the beamlets, and starting time and end time (t0*ij*, t1*ij*).

By comparing the calculated distributions (CDj) of cD(R)DHj with the acceptable band of variation (BV), it can be determined whether or not the calculated distribution (CDj) of cD(R)DHjj is comprised in the corresponding acceptable band of variation for the pre-defined confidence level (CLj). FIGS. 3(*b*) and 3(*c*) show an example of tentative statistical distributions (Tj) with associated confidence level (CLj) which yields calculated distributions (CDj) of cD(R)DHj comprised within the corresponding acceptable bands of variation (BV). By contrast, FIGS. 4(*b*) and 4(*c*) show an example of tentative statistical distribution (Tj) with associated confidence level (CLj) which yield calculated distributions (CDj) of cD(R)DHj extending beyond the corresponding acceptable bands of variation (BV) as indicated by the shaded areas and black arrows. For example, it can be seen in FIG. 4(*b*), that the cD(R)DHj–Run 1 already extends beyond the acceptable band of variation (BV). Calculation with the corresponding tentative statistical distribution can be stopped and a new tentative statistical distribution (T(j+1)) can be selected to repeat the N runs with values of the operating parameters randomly selected from the new tentative statistical distribution (T(j+1)).

The method of the present disclosure may conclude by setting a final statistical distribution (Tf) to the corresponding operating parameters with a final confidence level (CLf). If the N runs of calculated distributions (CDj) of cD(R)DHj are comprised within the corresponding acceptable band of variation (BV) with the pre-defined confidence level (CLj), for the given treatment plan (TP), the tentative statistical distribution (Tj) can be set as the final statistical distribution (i.e., Tf=Tj) with the final confidence level (CLf=CLj) to define the corresponding operating parameters. It can be concluded that, by implementing the final statistical distributions (Tf) of operating parameters, the particle accelerating system has a probability equal to the final confidence level (CU) of delivering the beamlets fulfilling the treatment plan (TP) with corresponding actual dose (rate) distribution histogram(aD(R)DH) comprised within the acceptable band of variation (BV), as shown e.g., in FIG. 1(*c*).

If, on the other hand, any one of the N runs of calculated dose (rate) distribution histogram (cD(R)DHj) extends beyond the boundaries of the corresponding acceptable bands of variation (BV) with the pre-defined confidence level (CLj) as shown e.g., in FIG. 4(*b*), a new tentative statistical distribution (T(j+1)) and/or a new confidence level (CL(j+1)) can be defined for one or more of the operating parameters and the cD(R)DHj can be calculated N times with N randomly selected values of each of the operating parameters. These operations can be repeated as often as necessary with new tentative statistical distributions (T(j+k)) of the operating parameters and/or with alternative confidence levels (CL(j+k)), until the calculated distributions (CD(j+k)) of cD(R)DHj(j+k) is comprised within the corresponding acceptable band of variation (BV) for the pre-defined confidence level (CLj) or (CL(j+k)). The final statistical distribution (Tf) can be set as being the tentative statistical distribution (T(j+k)) (i.e., Tf=T(j+k)) and the corresponding confidence level (CL(j+k)) can be set as the final confidence level (CLf=CL(j+k)), to define the corresponding operating parameters.

The new tentative statistical distributions (T(j+k)) defined in case the j+(k−1) preceding tentative statistical distributions did not yield calculated distributions included within the bands of variation (BV) surrounding target dose (rate) distribution histogram (tD(R)DH) for the pre-defined confidence level (CLj), can be selected as distributions having lower standard deviations (σj) (or variances $(\sigma j)^2$) than the corresponding preceding tentative statistical distributions (Tj+(k−1)).

Setting the final statistical distribution (Tf) for the corresponding operating parameters can be carried out by a human operator or automatically, by a processor.

Figure 2:
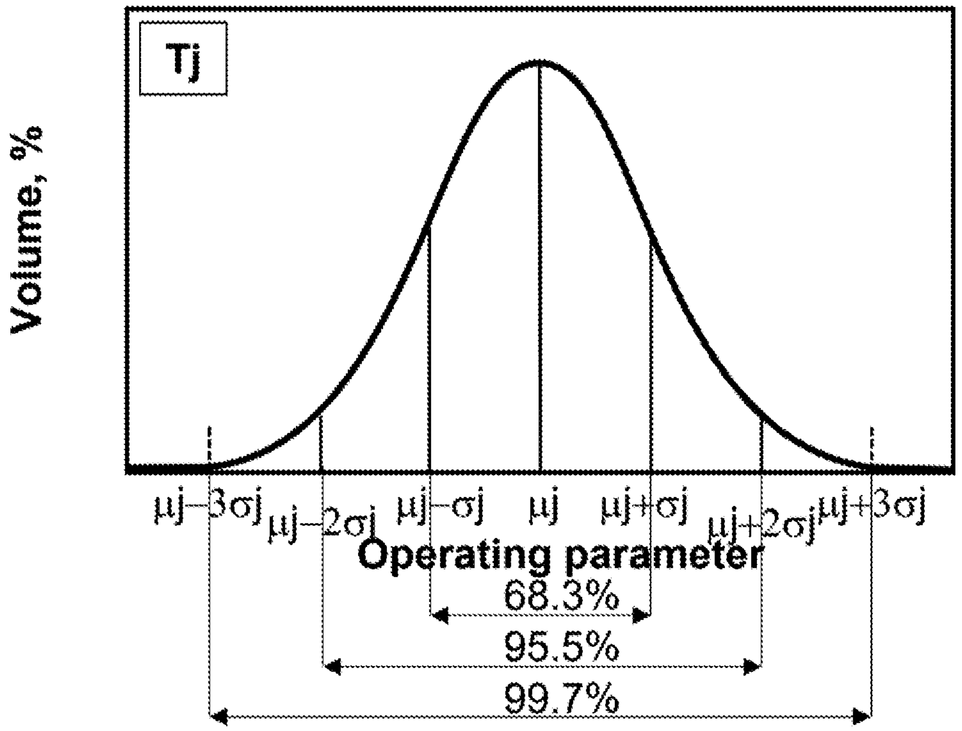
FIG. 2 shows a Gaussian distribution of an operating parameter of a given particle accelerating system.

The tentative statistical distributions (Tj) of each of the operating parameters may be Gaussian distributions. The values of the confidence levels (CL) may be comprised between 68% and 99.7%, or may be between 95.5 and 99% of the tentative statistical distribution. As shown in FIG. 2, a confidence level (CLj) of 68% corresponds to μj±σj. A confidence level (CLj) of 95% corresponds to μj±2σj and a confidence level of 99.7% of the tentative statistical distribution, corresponds to μj±3σj, wherein σj is the standard deviation of the corresponding tentative statistical distributions. For example, in terms of absolute deviations, the position (Xj) of a spot may, for example, vary by ±1 mm from the average value Rj of the Xj. The monitor unit (MUj) can for example vary by about 0.5% around the average value (Rj) of MUj. Note that the average values (Rj) and standard deviations (σj) of each operational parameter can be different for each beamlet (bi).

The particle accelerating system can be equipped with a cyclic check module configured for measuring at different intervals or continuously actual values of the monitor unit (MUai), the position (Xai), and of the starting time and end time ($t0_{ai}$, $t1_{ai}$) of the beamlets emitted by the particle accelerating system. A processor can be configured to determine whether any actual operating parameter falls outside of the corresponding final confidence level (CU) (shown in FIGS. 3(*a*) and 4(*a*), showing the confidence levels (CLj) spanning over a portion only of the statistical distributions (Tj)). In such case, an alarm can be triggered informing an operator of this event. As a safety measure, the processor can also be configured to stop the treatment as soon as an operating parameter falling outside of the confidence level (CLj) is detected.

The fact that one or more values of the actual operating parameters fall outside of the corresponding confidence levels (CLj) does not mean that the resulting actual dose (rate) distribution histogram (aD(R)DH) necessarily falls outside of the acceptable band of variation (BV). It could therefore be over-shooting to interrupt the treatment session simply because one actual value of any operating parameter falls outside of the corresponding confidence level (CLj), as it could perfectly yield a dose (rate) distribution histogram (D(R)DH) comprised within the acceptable band of variation (BV). The processor may be configured to calculate the cD(R)DH as soon as a measured actual value of an operating parameter falls outside of the corresponding confidence level (CLj) to determine whether or not the calculated cD(R)DH are comprised within the corresponding acceptable bands of variation (BV). The calculated dose (rate) distribution histogram (cD(R)DH) can be calculated based on the actual values of the operating parameters measured on the beamlets already delivered, including the parameter falling outside of the confidence level (CLj), and on the average values (Rj) of the operating parameters according to the final statistical distribution (Tf) for the beamlets which remain to be delivered to end the treatment session. If the calculated cD(R)DH falls outside of the acceptable band of variation (BV), the treatment session is stopped. If, on the other hand, the calculated cD(R)DH is within the acceptable band of variation (BV), the treatment session can proceed further. With this functionality of the processor, the risk of stopping a treatment session is further reduced.

This function does not take excessive calculating power, as it would concern only 100%−CLj % of the actual values of the operating parameters. For a confidence level (CLj) of 95% i.e., $\mu j \pm 2\sigma j$, there would be a probability of only 5% that a value of an operating parameter should fall outside of the confidence level (CLj) which the D(R)DH would have to be calculated for. For a confidence level of 99.7% of the tentative statistical distribution, i.e., $\mu j \pm 3\sigma j$, it would concern a probability of merely 0.3% where such calculation would be required.

In an embodiment, the treatment plan includes FLASH-RT, in that doses are to be deposited into at least a portion of the structure of interest at ultra-high deposition rates (UHDR) defined as a deposition rate greater than or equal to 1 Gy/s. In this embodiment, the planned parameters also comprise a beam current (I), whose values (Ij) used for calculating the calculated dose distribution histogram (=cD-DHj) and, in particular, the calculated dose rate distribution histogram (=cDRDHj) are randomly selected within a corresponding tentative statistical distribution (Tj) of the beam current (Ij).

Error Predicting Module

The present disclosure also provides an error predicting module configured to implement the method described above. The error predicting module comprises a memory comprising a plurality of tentative statistical distributions (Tj) for each operating parameter centered on a plurality of corresponding average values (Rj). It also comprises a user interface configured to enter,

- planned operators including a treatment plan (TP) including a planned position (Xpi), a planned monitor unit (MUpi), a planned beamlet scanning sequence, and planned starting time ($t0_{pi}$) and end time ($t1_{pi}$),
- the target dose (rate) distribution histogram (=tD(R)DH) and corresponding acceptable band of variation (BV), and
- for each beamlet, a first tentative statistical distribution (Tj) selected among or defined by entering values of the average values ($\mu j$) and standard deviations ($\sigma j$) from one or more of the plurality of tentative statistical distributions for each operating parameter, including at least a monitor unit (MUD, a position (Xj) of the beamlet, and starting time and end time ($t0_i$, $t1_i$), The error predicting module comprises a processor configured to,

- randomly select a value of the monitor unit (MUij), a value of the position (Xij) of the beamlet, values of the starting time and end time ($t0_{ij}$, $t1_{ij}$) comprised within the predefined confidence levels (CLj) of the corresponding tentative statistical distributions (Tj),
- calculate a calculated dose (rate) distribution histogram (=cD(R)Dj) with the values randomly selected,
- repeat the last two steps a statistically representative number of times (N) to yield the calculated distributions (CDj) of the calculated cD(R)Dj for each beamlet.

The processor can be further configured, in case the calculated distribution (CDj) of cD(R)Dj is not comprised within the corresponding acceptable band of variation with the pre-defined confidence level (CLj), to repeat the foregoing three steps with new tentative statistical distributions (T(j+k)) of the operating parameters, until the calculated distributions (CDj) of cD(R)Dj is comprised within the corresponding acceptable bands of variation with the pre-defined confidence level (CLj).

Flowchart (FIG. 6)

FIG. 6 shows a flowchart illustrating various steps of an embodiment of the present disclosure. The requirements of a treatment plan (TP) (shown in step (1) of FIG. 6) are translated into planned parameters for all the beamlets (shown in step (2) of FIG. 6). One or more target dose (rate) distribution histograms (tD(R)DH) are defined (shown in step (3) of FIG. 6) with their corresponding acceptable bands of variation (BV) (shown in step (4) of FIG. 6). As defined above, the dose (rate) distribution histograms (D(R)DH) can include non-exhaustively, the dose volume histogram (DVDH), the dose rate volume histogram (DRVH), or the differential dose rate distribution histogram (DDRH), and the like.

The particle accelerating system is simulated (shown in step (5) of FIG. 6), by defining a first tentative statistical distribution (Tj) and a corresponding confidence level (CLj) (show in steps (6) and (7) of FIG. 6). A value of each operational parameter is randomly selected within the confidence level (CLj) of the tentative statistical distributions (Tj) (shown in step (8) of FIG. 6) and the resulting cD(R)DHj−Run (x=1) is calculated (shown in step (9) of FIG. 6). If the calculated CD(R)DH−Run (x=1) is not within the acceptable band of variation (BV) a new tentative statistical distribution (T(j+1)) is selected with a corresponding confidence level (CL(j+1)) (show in steps (10) and (11) of FIG. 6), and steps (7) to (10) are repeated. If, on the other hand, the calculated CD(R)DH−Run (x=1) is within the acceptable band of variation (BV), a new value of each operational parameter is randomly selected a statistically representative number of times (N) within the confidence level (CLj) of the tentative statistical distributions (Tj) (shown in steps (11), (12) and (8) of FIG. 6) and steps (8) to (10) are repeated. When all N Runs x yielding calculated CD(R)DH−Run (x=1 to N) are within the acceptable band of variation (BV), the corresponding tentative statistical distribution (Tj) can be set as the final statistical distribution (Tf) (show in step (13) of FIG. 6). The particle accelerating system can be programmed with the operational parameters according to the corresponding final statistical distributions (Tf). With such programming, the particle accelerating system has a probability of CLj % of delivering beamlets satisfying the treatment plan without interruption of the treatment session.

The method of the present disclosure can be implemented with a single calculated dose (rate) histogram (cD(R)DH) or with several histograms which must all be within the corresponding acceptable bands of variation (BV) to set the final statistical distribution (Tf). If a first tentative statistical distribution (Tj) yields one histogram (e.g., cDVH) enclosed within the corresponding acceptable band of variation (BV) but another histogram (e.g., cDRVH) extending beyond the acceptable band of variation (BV), a new tentative statistical distribution (T(j+1)) is selected and the method is carried out again, until a tentative statistical distribution (T(j+k)) is found that fits all the required histograms into the corresponding acceptable bands of variation (BV). Dose rate related histograms (e.g., DRVH, DDRH) are particularly useful for treatment plans comprising beamlets to be emitted in FLASH-mode for depositing doses at ultra-high deposition rates into selected spots of the structure of interest.

| Ref | Description |
|---|---|
| BV | Band of variation |
| CDj | Calculated distribution of cDVHj and cDVRHj |
| D(R)DH | Dose (rate) distribution histogram (D(R)DH) includes both “dose distribution histograms (DDH)” and “dose rate distribution histograms (DRDH).” |
| cD(R)Dj | Calculated dose (rate) distribution histogram of beamlet Si with tentative statistical distribution Tj |
| cDVH | Calculated dose volume histogram of beamlet Si with tentative statistical distribution Tj |
| cDRVH | Calculated dose rate volume histogram of beamlet Si with tentative statistical distribution Tj |
| cD(R)Dj0 | Minimum calculated dose (rate) distribution histogram |
| cD(R)Dj1 | Maximum calculated dose (rate) distribution histogram |
| CLj | Confidence level |
| CLf | Final confidence level |
| Dj | Beamlet size |
| DRj | Dose deposition rate |
| x | x = 1 − N Runs |
| j, k | Identifies one tentative statistical distribution of an operational parameter |
| MUai | Actual monitor unit of a beamlet Si as delivered by the particle accelerator |
| MUj | Monitor unit distribution of a beamlet Si according to the tentative statistical distribution |
| MUij | Random value from the monitor unit distribution of a beamlet Si |
| MUpi | Planned monitor unit of a beamlet Si |
| PBS | Pencil Beam Scanning |
| Si | Beamlet |
| Tj, T(j + k) | Tentative statistical distribution of an operational parameter |
| Tf | Final statistical distribution of an operational parameter |
| TP | Treatment plan |
| t0aj | Actual starting time of a bemlet Si |
| t0j | Starting time distribution of a beamlet Si according to the tentative statistical distribution |
| t0ij | Random value from the starting time distribution of a beamlet Si |
| t0pi | Planned starting time of a beamlet Si |
| t1ai | Actual end time of a bemlet Si |
| t1i | End time distribution of a beamlet Si according to the tentative statistical distribution |
| t1ij | Random value from the end time distribution of a beamlet Si |
| t1pi | Planned end time of a beamlet Si |
| tD(R)DH | Target dose (rate) distribution histogram of beamlet Si with tentative statistical distribution Tj |
| tDVH | Target dose volume histogram of beamlet Si with tentative statistical distribution Tj |
| tDRVH | Target dose rate volume histogram of beamlet Si with tentative statistical distribution Tj |
| Xai | Actual position of a beamlet Si |
| Xi | Position of a beamlet Si |
| Xij | Random value from the position of a beamlet Si |
| Xpi | Planned position of a beamlet Si |
| (X, Y) | Plane normal to the irradiation axis (Z) |
| Z | Irradiation axis |
| μj | Average value of an operational parameter distribution of beamlet Si |
| σj | Standard deviation of an operational parameter distribution of beamlet Si |

What is claimed is:

1. A method for obtaining tolerance values of operating parameters of a particle accelerating system providing a beam, formed by a plurality of beamlets of particles accelerated along an irradiation axis, to deposit doses by pencil beam scanning into a structure of interest of a patient in a treatment plan, the method comprising:

obtaining:

a plurality of planned parameters in the treatment plan, the plurality of planned parameters including:

a planned position of each of an array of beamlets on a plane normal to the irradiation axis, a planned monitor of each of the array of beamlets, and a planned beamlet scanning sequence over the planned positions of the array of beamlets;

a planned starting time and an end time to deliver each of the array of beamlets;

information about one or more tissues of the structure of interest in the treatment plan;

values of at least one or more of target dose or dose rate distribution histograms for the structure of interest with a treatment with the plurality of planned parameters in the treatment plan; and bands of variation, wherein the at least one or more of target dose or dose rate distribution histograms are allowed to vary within the bands of variation;

obtaining a first tentative statistical distribution of operating parameters of the particle accelerating system configured to center on corresponding average values representative of performance of the particle accelerating system and define a first confidence level of the first tentative statistical distribution, wherein the operating parameters comprise;

a monitor of each of the array of beamlets, a position of each of the array of beamlets, and a starting time and an end time to deliver each of the array of beamlets;

randomly selecting, from the corresponding first tentative statistical distributions within the first confidence levels, values of the operating parameters, the values of the operating parameters including a value of the monitor, a value of the position, and a value of of the starting time and a value of the end time for each of the array of beamlets;

calculating at least one or more of calculated dose or dose rate distribution histograms based on the values of the operating parameters;

repeating the randomly selecting values of the operating parameters and the calculating the at least one or more of calculated dose or dose rate distribution histograms a predetermined number of times to obtain calculated distributions characterizing the at least one or more of calculated dose or dose rate distribution histograms for the values of the operating parameters;

comparing the calculated distributions of the at least one or more of calculated dose or dose rate distribution histograms with the corresponding bands of variation;

determining whether the calculated distributions of the at least one or more of calculated dose or dose rate distribution histograms are within the corresponding bands of variation within the first confidence level; and setting a final statistical distribution with a final confidence level for corresponding operating parameters by:

if the calculated distributions of the at least one or more of calculated dose or dose rate distribution histograms are within the corresponding bands of variation with the first confidence level, setting the first tentative statistical distribution as the final statistical distribution and the first confidence level as the corresponding final confidence level to define the corresponding operating parameters; and if one of the at least one or more of calculated dose or dose rate distribution histograms extends beyond the corresponding bands of variation:

obtaining a second tentative statistical distribution of the operating parameters or selecting a second confidence level, randomly selecting second values of the operating parameters based on the second tentative statistical distribution or the second confidence level, and calculating at least one or more of second calculated dose or dose rate distribution histograms based on the second values of the operating parameters, wherein calculated distributions of the at least one or more of second calculated dose or dose rate distribution histograms are within the corresponding bands of variation;

setting the second tentative statistical distribution as the final statistical distribution; and setting the corresponding second confidence level as the final confidence level to define the corresponding operating parameters.

2. The method of claim 1, wherein setting the final statistical distribution for the corresponding operating parameters is performed by a processor.

3. The method of claim 1, wherein the second tentative statistical distributions have lower standard deviations than the first tentative statistical distributions.

4. The method of claim 1, wherein;

the first tentative statistical distributions of the operating parameters are Gaussian distributions; and the value of the first confidence level is between 68% and 99.7% of the first tentative statistical distribution, wherein:

a first confidence level of 68% corresponds to $\mu j+\sigma j$, a first confidence level of 95% corresponds to $\mu j\pm 2\sigma j$, and a first confidence level of 99.7% corresponds to $\mu j\pm 3\sigma j$, wherein $\mu j$ and $\sigma j$ are respectively an average value and a standard deviation of one of the corresponding first tentative statistical distributions.

5. The method of claim 4, wherein the average values and standard deviations of the operating parameters are different for each of the array of beamlets.

6. The method of claim 4, wherein the value of the first confidence level is between 95.5% and 99% of the first tentative statistical distribution.

7. The method of claim 1, further comprising:

measuring at different intervals or continuously values of the operating parameters including the monitor, the position, and of the starting time and end time of the beamlets emitted by the particle accelerating system.

8. The method of claim 7, wherein the particle accelerating system includes a processor, the method further comprising:

comparing, by the processor, the actual values of the operating parameters with the corresponding first confidence level; and stopping, by the processor, a treatment session when one actual value of an operating parameter falls outside of the corresponding final confidence level.

9. The method of claim 1, wherein the planned parameters comprise a planned beamlet size, the method further comprising:

randomly selecting values of the planned beamlet size within a corresponding tentative statistical distribution of the beamlet size for calculating the at least one or more of calculated dose or dose rate distribution histograms.

10. The method of claim 1, wherein:

the distributions of the at least one or more of calculated dose or dose rate distribution histograms are defined by a corresponding area between a minimum calculated dose or dose rate distribution histogram and a maximum calculated dose or dose rate distribution histogram, wherein:

the minimum calculated dose or dose rate distribution histogram is defined by the lowest values of the at least one or more of calculated dose or dose rate distribution histograms calculated with the first confidence level from the values of the monitor, position of the beamlets, and starting time and end time; and the maximum calculated dose or dose rate distribution histogram is defined by the highest values of the at least one or more of calculated dose or dose rate distribution histograms calculated with the first confidence level from the values of the monitor, position of the beamlets, and starting time and end time.

11. The method of claim 1, wherein the treatment plan includes depositing doses into at least a portion of the structure of interest at an ultra-high deposition rate (UHDR), the UHDR being a deposition rate greater than or equal to 1 Gy/s.

12. The method of claim 1, wherein the plurality of planned parameters comprise a planned beam current, the method further comprising:

randomly selecting values of the planned beam current within a corresponding tentative statistical distribution of the beam current for calculating the at least one or more of calculated dose or dose rate distribution histograms.

13. The method of claim 1, wherein:

the one or more distribution histograms of dose are one or more dose volume histograms, the one or more distribution histograms of dose rate are one or more dose rate volume histograms or one or more differential dose rate histograms, and the one or more distribution histograms of dose and dose rate are:

one or more dose volume histograms or one or more differential dose histograms, and one or more dose rate volume histograms or one or more differential dose rate histograms.

14. An error predictor for a particle accelerating system, the error predictor comprising:

a memory storing a plurality of first tentative statistical distributions for a plurality of operating parameter centered on a plurality of corresponding average values representative of performance of the particle accelerating system;

a user interface configured to receive:

a treatment plan including one or more target dose or dose rate distribution histograms, and corresponding acceptable bands of variation;

a planned starting time and a planned end time, or a selection of the planned starting time and the planned end time from the memory, to deliver each of an array of beamlets;

for each of the array of beamlets, a first tentative statistical distribution for the plurality of operating parameters, or a selection of the first tentative statistical distribution from the memory, the plurality of the operating parameters including a monitor, a position of the beamlet, and a starting time and an end time; and a confidence level on the plurality of operating parameters;

a processor configured to:

randomly select a value of the monitor, a value of the position of the beamlet, and values of the starting time and the end time within the confidence levels of the corresponding first tentative statistical distributions;

calculate at least one or more of calculated dose or dose rate distribution histograms with the values of the monitor, the position of the beamlet, and the starting time and the end time; and repeat the randomly selecting and the calculating a predetermined number of times to obtain calculated distributions of the at least one or more of calculated dose or dose rate distribution histograms for the array of beamlets; and if one of the calculated distributions of corresponding at least one or more of calculated dose or dose rate distribution histograms is not within the corresponding bands of variation with the confidence level, repeat the randomly selecting, the calculating, and the repeating with second tentative statistical distributions of the operating parameters, until the calculated distributions of the at least one or more of calculated dose or dose rate distribution histograms are within the corresponding bands of variation with the confidence level.

* * * * *